(12) United States Patent
Lin et al.

(10) Patent No.: US 9,955,735 B2
(45) Date of Patent: May 1, 2018

(54) ELECTRONIC CIGARETTE CAPABLE OF TEMPERATURE CONTROL AND TEMPERATURE CONTROL METHOD THEREFOR

(71) Applicant: Guangrong Lin, Shenzhen, Guangdong (CN)

(72) Inventors: Guangrong Lin, Guangdong (CN); Xianbin Zheng, Guangdong (CN); Xindi Hu, Guangdong (CN)

(73) Assignee: Guangrong Lin, Shenzhen (CN)

( * ) Notice: Subject to any disclaimer, the term of this patent is extended or adjusted under 35 U.S.C. 154(b) by 0 days. days.

(21) Appl. No.: 15/325,725

(22) PCT Filed: Sep. 2, 2015

(86) PCT No.: PCT/CN2015/088819
§ 371 (c)(1),
(2) Date: Jan. 12, 2017

(87) PCT Pub. No.: WO2016/062167
PCT Pub. Date: Apr. 28, 2016

(65) Prior Publication Data
US 2017/0164658 A1  Jun. 15, 2017

(30) Foreign Application Priority Data

Oct. 24, 2014  (CN) .......................... 2014 1 0574198

(51) Int. Cl.
*A24F 47/00* (2006.01)
*H05B 1/02* (2006.01)

(52) U.S. Cl.
CPC ......... *A24F 47/008* (2013.01); *H05B 1/0244* (2013.01); *H05B 2203/021* (2013.01)

(58) Field of Classification Search
None
See application file for complete search history.

(56) References Cited

U.S. PATENT DOCUMENTS 4,073,077 A   2/1978  Essel et al.
4,369,847 A   1/1983  Mizunuma
(Continued)

FOREIGN PATENT DOCUMENTS

CN   203618789 U   6/2014
CN   203630559 U   6/2014
(Continued)

OTHER PUBLICATIONS

International search report of PCT Patent Application No. PCT/CN2015/088819 dated Nov. 9, 2015.

*Primary Examiner* — Tho D Ta

(57) ABSTRACT

An electronic cigarette capable of temperature control and a temperature control method therefor, the electronic cigarette comprises a casing (10), a liquid storage device (101) within the casing (10), an atomizing assembly, a power supply (102), and a circuit control board (103) having a smoking switch SW, the atomizing assembly comprises a heating unit and leads thereof made from thermo-sensitive material whose resistance varies along with the temperature in certain proportion, the circuit control board (103) comprises a power supply managing module (104) which determines temperature of the heating unit and leads thereof by continuously detecting their resistance when the smoking switch SW on, and sends corresponding control signal to make the heating unit and leads thereof connect to/disconnect from the power supply (102) to achieve temperature control, pernicious gas and burnt matter produced by heating unit dry-burn caused by lack of e-liquid threatening users' health is prevented.

11 Claims, 9 Drawing Sheets

(56) References Cited

U.S. PATENT DOCUMENTS

| | | | |
|---|---|---|---|
| 5,392,538 A | 2/1995 | Geerligs et al. | |
| 5,595,007 A | 1/1997 | Biance | |
| 6,408,548 B1 | 6/2002 | Altheide | |
| 2014/0014126 A1* | 1/2014 | Peleg | A24F 47/008 131/329 |
| 2015/0208729 A1* | 7/2015 | Monsees | A24F 47/008 131/329 |
| 2015/0305409 A1* | 10/2015 | Verleur | H02J 7/0022 131/329 |
| 2015/0335074 A1* | 11/2015 | Leung | A61M 15/06 131/328 |
| 2015/0359263 A1* | 12/2015 | Bellinger | A24F 47/008 392/394 |
| 2016/0100632 A1* | 4/2016 | Debono | A24F 47/008 219/494 |

FOREIGN PATENT DOCUMENTS

| | | |
|---|---|---|
| CN | 203643774 U | 6/2014 |
| CN | 104319732 A | 1/2015 |
| CN | 204191588 U | 3/2015 |

\* cited by examiner

| Time (seconds) | Regular Surface temperature of the heating coil in normal smoking status (°C) | Surface temperature of the heating coil dry burning due to lack of e-liquid (°C) |
|---|---|---|
| 1 | 85 | 90 |
| 2 | 105 | 176 |
| 3 | 112 | 260 |
| 4 | 125 | 322 |
| 5 | 128 | 400 |
| 6 | 132 | 485 |
| 7 | 139 | 573 |
| 8 | 141 | 660 |

Figure 1 (Prior Art)

| Time (seconds) | Temperature control | |
|---|---|---|
| | Surface temperature of the heating coil in normal smoking status (°C) | Surface temperature of the heating coil dry burning due to lack of e-liquid (°C) |
| 1 | 85 | 90 |
| 2 | 105 | 176 |
| 3 | 112 | 210 |
| 4 | 125 | 150 |
| 5 | 128 | 80 |
| 6 | 132 | 60 |
| 7 | 139 | 50 |
| 8 | 141 | 40 |

Figure 5

| Temperature (°C) | ① Resistance of thermo-sensitive heating coil (Ω) | ② Resistance of regular heating coil (Ω) |
|---|---|---|
| 0-100 | 2.85 | 2.85 |
| 101-150 | 2.9 | 2.85 |
| 151-200 | 2.95 | 2.86 |
| 201-250 | 3.05 | 2.86 |
| 251-300 | 3.1 | 2.86 |
| 301-350 | 3.15 | 2.86 |
| 351-400 | 3.2 | 2.87 |
| 401-500 | 3.25 | 2.87 |
| 501-550 | 3.3 | 2.87 |
| 551-600 | 3.35 | 2.87 |
| 601-650 | 3.4 | 2.87 |
| 651-700 | 3.45 | 2.88 |
| 701-750 | 3.5 | 2.88 |
| 751-800 | 3.55 | 2.89 |
| 801-850 | 3.6 | 2.89 |
| 851-900 | 3.65 | 2.9 |
| 901-950 | 3.7 | 2.91 |
| 951-1000 | 3.75 | 2.92 |

Figure 7

ELECTRONIC CIGARETTE CAPABLE OF TEMPERATURE CONTROL AND TEMPERATURE CONTROL METHOD THEREFOR

FIELD OF THE INVENTION

The present invention relates to the field of electronic cigarettes, in particular, to an electronic cigarette capable of temperature control and a temperature control method therefor.

BACKGROUND OF THE INVENTION

Generally, electronic cigarettes emit vapor to cater users by utilizing atomizers to heat and atomize e-liquid. As people's awareness of health increasing, the harm of tobacco is generally recognized thus electronic cigarettes become widely used instead of traditional cigarettes gradually.

When e-liquid is used up, electronic cigarettes of the prior art proceed to work only when the liquid storage device is replaced or replenished with e-liquid manually. Moreover, if a user keeps using the electronic cigarette in which e-liquid is nearly used up without adding e-liquid or replacing the liquid storage device, the electronic cigarette would be burn out and scrapped, and worse than that, when e-liquid is used up or insufficient, the heating unit tends to dry burn and produces pernicious gas and burnt matter which would be inhaled by the user and causes health problems. Referring to FIGS. 1-2, a table and a curve graph both show the comparison of the surface temperature change of the heating coil over time in normal status and in e-liquid shortage status. It can be seen from the figures that when e-liquid is used up, the surface temperature of the heating coil rises fiercely, which easily leads to burnout of the electronic cigarette and harm to user's health.

SUMMARY OF THE INVENTION

The present invention aims to provide an electronic cigarette capable of temperature control to overcome disadvantages above. The electronic cigarette capable of temperature control is able to monitor the temperature of the heating unit and the leads thereof, so as to protect the electronic cigarette from dry burning.

The present invention provides an electronic cigarette capable of temperature control, comprising a casing, a liquid storage device within the casing, an atomizing assembly, a power supply, and a circuit control board provided with a smoking switch SW. The advancement of the electronic cigarette of the present invention is as follows: the atomizing assembly comprises a heating unit and leads thereof, material of the heating unit and/or the leads is thermo-sensitive whose resistance varies along with the temperature in certain proportion, the circuit control board comprises a power supply managing module, when the smoking switch SW is on, the power supply managing module determines the corresponding temperature of the heating unit and the leads thereof by continuously detecting resistance of them, and sends corresponding control signals to make the heating unit and leads thereof connect to or disconnect from the power supply.

Preferably, the power supply managing module further comprises a chip U1, a triode Q4, a metal oxide semiconductor field effect transistor M1, a third resistor R3, a fifth resistor R5, a sixth resistor R6, wherein the chip U1 has a number of pins, wherein a first pin is an on/off signal end KEY 1, a fourth pin is a power supply signal end BT+, a ninth pin is a control signal end HOT, a thirteenth pin is a grounding end and a sixteenth pin is a signal detecting end FB;

one end of the smoking switch SW is grounded while the other end thereof is connected to the end KEY 1;

one end of the third resistor R3 is connected to the end HOT while the other end thereof is connected to the base of the triode Q4; the emitter of the triode Q4 is grounded and between the base and the emitter thereof is provided a fourth resistor R4, the collector of the triode Q4 is connected to both the gate of the metal oxide semi-conductor field effect transistor M1 and one end of the fifth resistor R5, while both the other end of R5 and the source of the metal oxide semi-conductor field effect transistor M1 are connected to the end BT+;

the drain of the metal oxide semi-conductor field effect transistor M1 also acts as an end F+, one end of the heating unit and leads thereof is connected to the end F+ while the other end thereof is grounded; one end of the sixth resistor R6 is grounded while the other end thereof and the drain of the metal oxide semi-conductor field effect transistor M1 are both connected to the end FB.

Preferably, the power supply managing module further comprises a seventh resistor R7 and a capacitor C1, wherein one end of the seventh resistor R7 is connected to the end FB while the other end thereof and one end of the capacitor C1 are connected and grounded, and the other end of the capacitor C1 is connected to the end BT+.

Preferably, the power supply managing module further comprises a first resistor R1, a second resistor R2, a first light emitting diode D1 and a second light emitting diode D2; the chip U1 further comprises a fifth pin and a sixth pin, wherein the fifth pin is connected to one end of the first resistor R1 and the other end of the first resistor R1 is connected to one end of the first light emitting diode D1, similarly, the sixth pin is connected to one end of the second resistor R2 and the other end of the second resistor R2 is connected to one end of the second light emitting diode D2, the other end of the first light emitting diode D1 and that of the second light emitting diode D2 are both grounded; when the power supply managing module detects a signal indicating temperature of the heating unit and leads thereof is normal, the fifth pin of the chip U1 is powered to light the first light emitting diode D1 to indicate the electronic cigarette is in normal smoking status; otherwise, when the power supply managing module detects a signal indicating abnormal temperature of the heating unit and leads thereof and disconnects them from the power supply, the sixth pin of the chip U1 is powered to light the second light emitting diode D2 to indicate a malfunction of dry burn is occurred in the electronic cigarette.

Preferably, the material of the heating unit and/or the leads thereof is thermo-sensitive material with a positive temperature coefficient.

Preferably, the atomizing assembly further comprises a liquid guiding element for guiding the e-liquid from the liquid storage device and the heating unit is a heating coil abutting the liquid guiding element.

The present invention also discloses a method for controlling the temperature of the heating unit within the electronic cigarette above, and thereby the control of temperature of the electronic cigarette is achieved and the problem of over-temperature due to dry-burn of the heating coil caused by the lack of e-liquid is solved. Specifically, the method comprises the following steps:

S1: turning a smoking switch SW off and disconnecting a circuit control board from a power supply when the electronic cigarette is not in service;

S2: turning on the smoking switch SW when the user begins to smoke, sending a control signal via the end HOT according to a signal at an end KEY1 by a chip U1, connecting a heating coil R to the power supply via a metal oxide semi-conductor field effect transistor M1, starting to read electronic signals about temperature at an end FB by the chip U1;

S3: atomizing the e-liquid by the heating coil R when there is e-liquid in an atomizing assembly, during the process, the temperature of the heating coil R is stable and its resistance generally remains constant, a electronic signal at the end FB detected by the chip U1 stays constant, and the control signal sent via the end HOT by the chip U1 stays constant, and keeping providing vapor to the user;

S4: controlling the metal oxide semi-conductor field effect transistor M1 by the chip U1 via the end HOT to disconnect the heating coil R from the power supply and stopping providing vapor to the user when the e-liquid in the atomizing assembly is used up or in shortage, the surface of the heating coil R dry burns, the temperature thereof goes up fiercely, the resistance of the heating coil R rises rapidly because the heating coil R is made from thermo-sensitive material with a positive temperature coefficient and a change of the electronic signal about temperature at the end FB is detected by the chip U1, and then temperature of the heating coil R starts to go down;

S5: cutting off the power supply immediately even if the smoking switch SW is turned on again by the user and the power supply is restored provisionally before the temperature of the heating coil R goes down to a preset threshold temperature 210° C. and e-liquid is supplemented to the atomizing assembly, as the electronic signal about temperature at the end FB detected by the chip U1 still is abnormal;

S6: supplying power to the heating coil R to atomizes the e-liquid normally till the temperature of the heating coil R goes down below the preset threshold temperature 210° C., the e-liquid is supplemented to the atomizing assembly, the heating coil R returns its normal resistance and the user proceeds to smoke, and continuing supplying power to the heating coil R if the chip U1 detects the electronic signal about temperature at the end FB is normal.

Besides, the present invention further discloses another method for controlling the temperature of the electronic cigarette above, and thereby the control of temperature of the heating unit within the electronic cigarette is achieved and the problem of over-temperature due to dry-burn of the heating coil caused by the lack of e-liquid is solved. Specifically, the method comprises the following steps:

S1: turning a smoking switch SW off and disconnecting a circuit control board from a power supply when the electronic cigarette is not in service;

S2: turning on the smoking switch SW when the user begins to smoke, sending a control signal via the end HOT according to a signal at an end KEY1 by a chip U1, connecting a heating coil R to the power supply via a metal oxide semi-conductor field effect transistor M1, starting to read electronic signals about temperature at an end FB by the chip U1;

S3: atomizing the e-liquid by the heating coil R when there is e-liquid in an atomizing assembly, during the process, the temperature of the heating coil R is stable and its resistance generally remains constant, a rate of temperature change at the end FB detected by the chip U1 is lower than a preset rate of temperature change, and the control signal sent via the end HOT by the chip U1 stays constant, and keeping providing vapor to the user;

S4: controlling the metal oxide semi-conductor field effect transistor M1 by the chip U1 via the end HOT to disconnect the heating coil R from the power supply and stopping providing vapor to the user when the e-liquid in the atomizing assembly is used up or in shortage, the surface of the heating coil R dry burns, the temperature thereof goes up fiercely, the resistance of the heating coil R rises rapidly because the heating coil R is made from thermo-sensitive material with a positive temperature coefficient and the rate of temperature change at the end FB detected by the chip U1 exceeds the preset rate of temperature change, and then temperature of the heating coil R starts to go down;

S5: cutting off the power supply immediately even if the smoking switch SW is turned on again by the user and the power supply is restored provisionally before the rate of temperature change of the heating coil R goes down below the preset rate of temperature change and e-liquid is supplemented to the atomizing assembly, as the rate of temperature change at the end FB detected by the chip U1 still exceeds the preset rate of temperature change;

S6: supplying power to the heating coil R to atomizes the e-liquid normally till the rate of temperature change of the heating coil R goes down below the preset rate of temperature change, the e-liquid is supplemented to the atomizing assembly, the heating coil R returns its normal resistance and the user proceeds to smoke, and continuing supplying power to the heating coil R if the chip U1 detects rate of temperature change at the end FB is normal.

According to the preceding circuit structure of the present invention, the resistance of the heating unit and the leads thereof can be detected because of the circuit structure including the chip U1, the triode Q4 and the metal oxide semi-conductor field effect transistor M1, and detection of the change of temperature can be achieved on the basis of the change of the resistance, therefore, the present invention does well in temperature control of heating unit within the electronic cigarette and the problem of over-temperature due to dry-burn of the heating unit caused by the lack of e-liquid is effectively prevented; besides, it brings no impact to the size of the electronic cigarette owing to its simple circuit, so it is adapted to be applied inside the electronic cigarette so as to protect both electronic cigarette itself and the human health; furthermore, the temperature control method of the present invention limits the temperature of the heating unit to under the threshold temperature, so that the problem of over-temperature of the heating unit can be avoid without any impact to normal use.

BRIEF DESCRIPTION OF THE DRAWINGS

FIG. 1 is a table showing the temperature change of a heating coil in an electronic cigarette according to the prior art.

FIG. 5 is a table showing the temperature change of a heating coil in an electronic cigarette capable of temperature control according to the present invention.

FIG. 7 is a table showing a comparison between resistance of the heating coil according to the present invention and resistance of the regular heating coil.

DETAILED DESCRIPTION OF THE PREFERRED EMBODIMENTS

Figure 2:
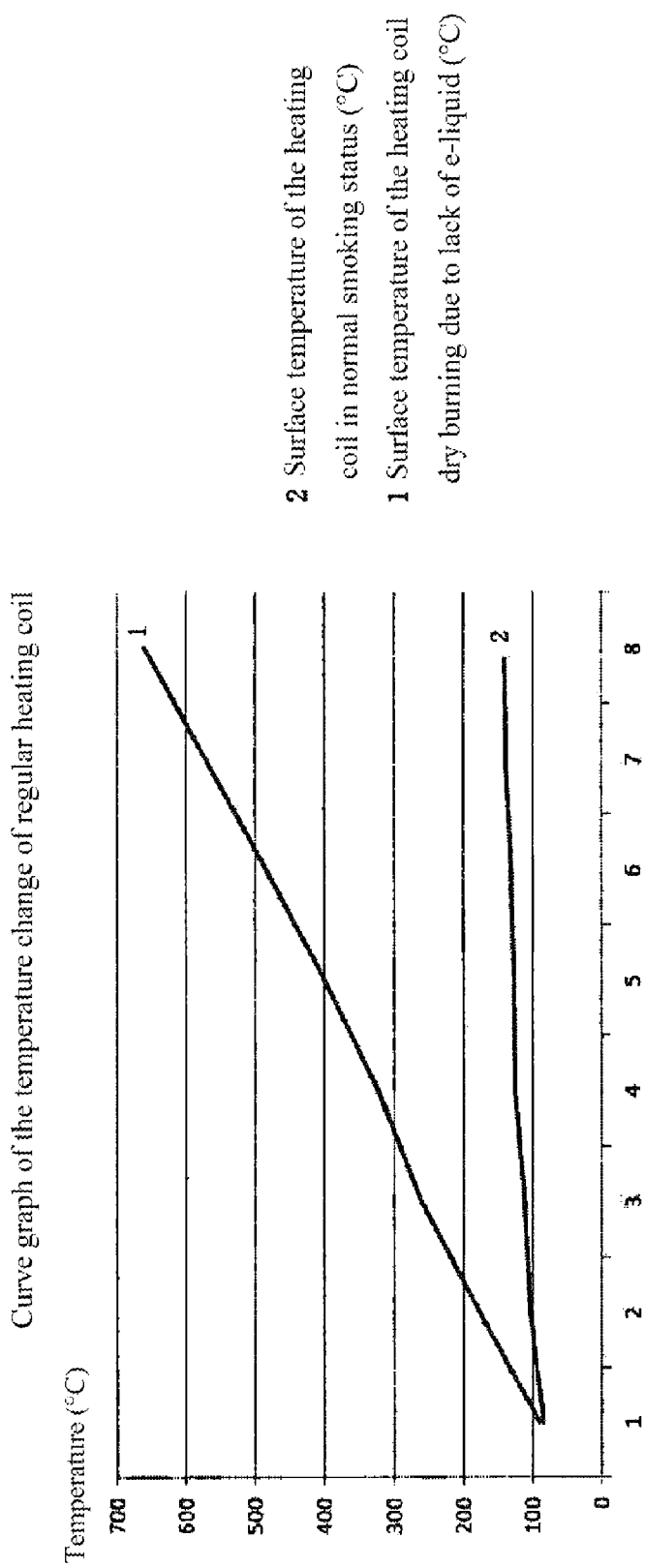
FIG. 2 is a curve graph showing the temperature change of a heating coil in an electronic cigarette according to the prior art.
Figure 3:
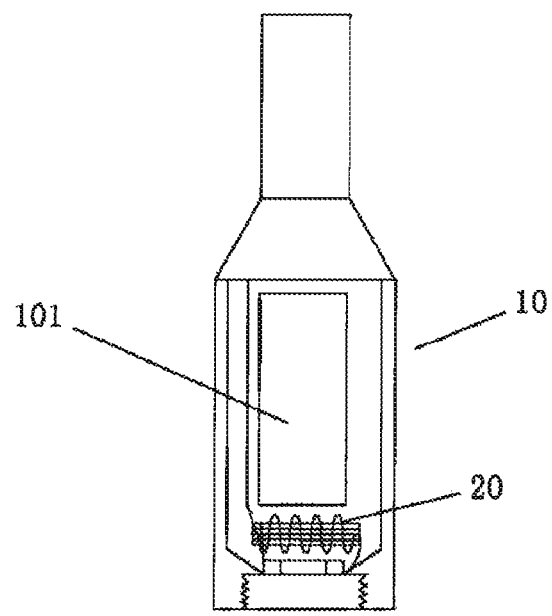
FIG. 3 is a structural diagram of an electronic cigarette capable of temperature control according to the present invention.
Figure 3:
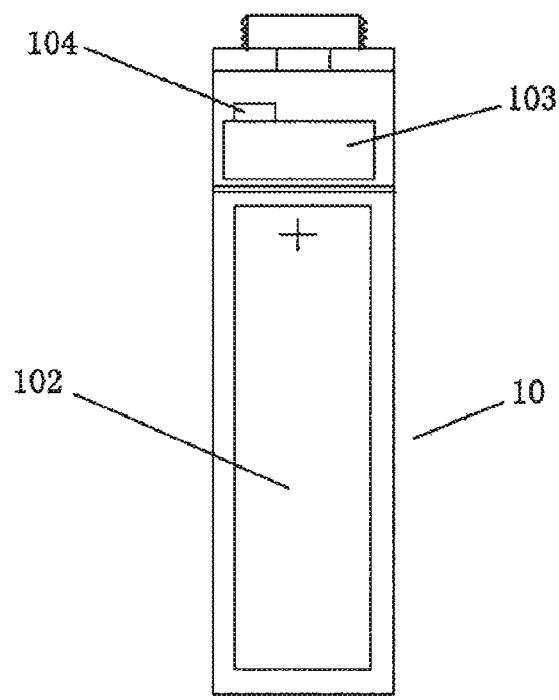
Figure 4:
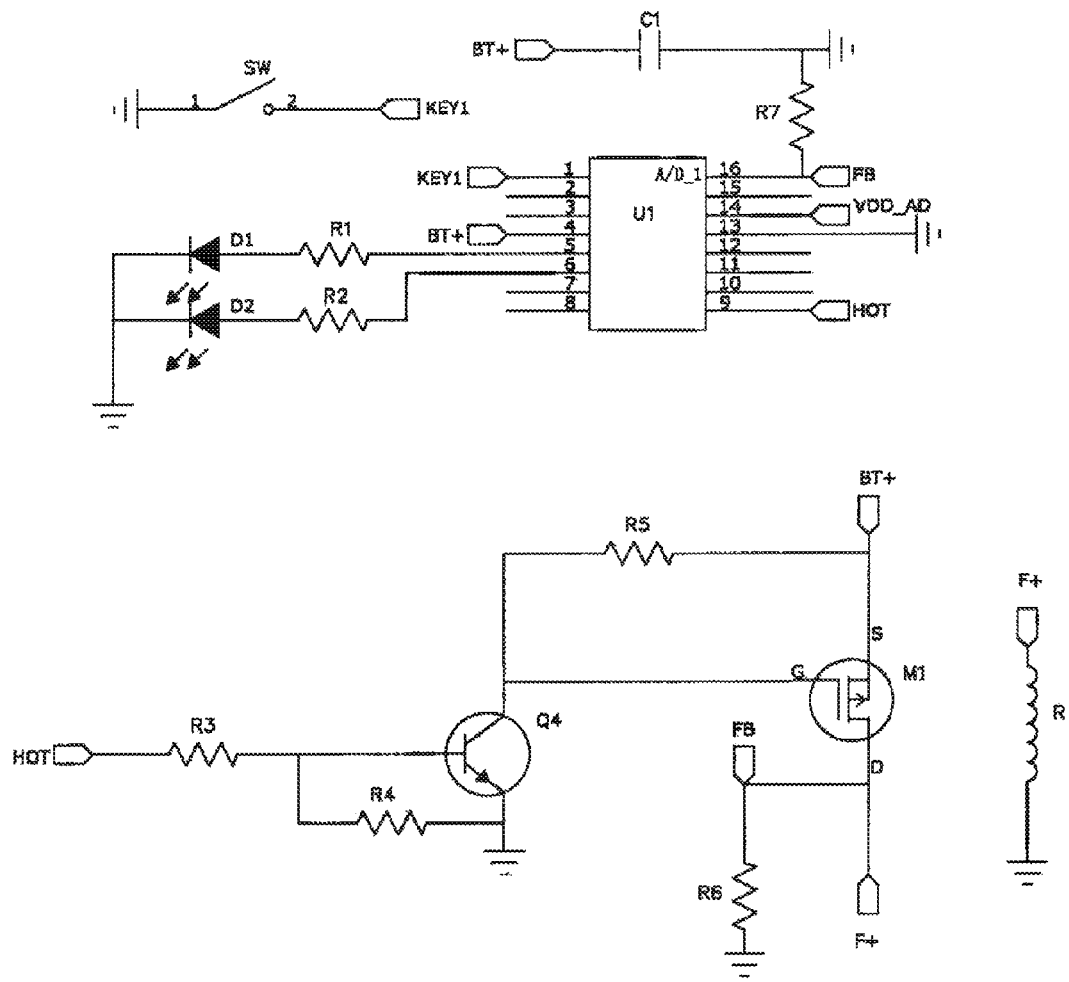
FIG. 4 is a circuit diagram of an electronic cigarette capable of temperature control according to the present invention.
Figure 6:
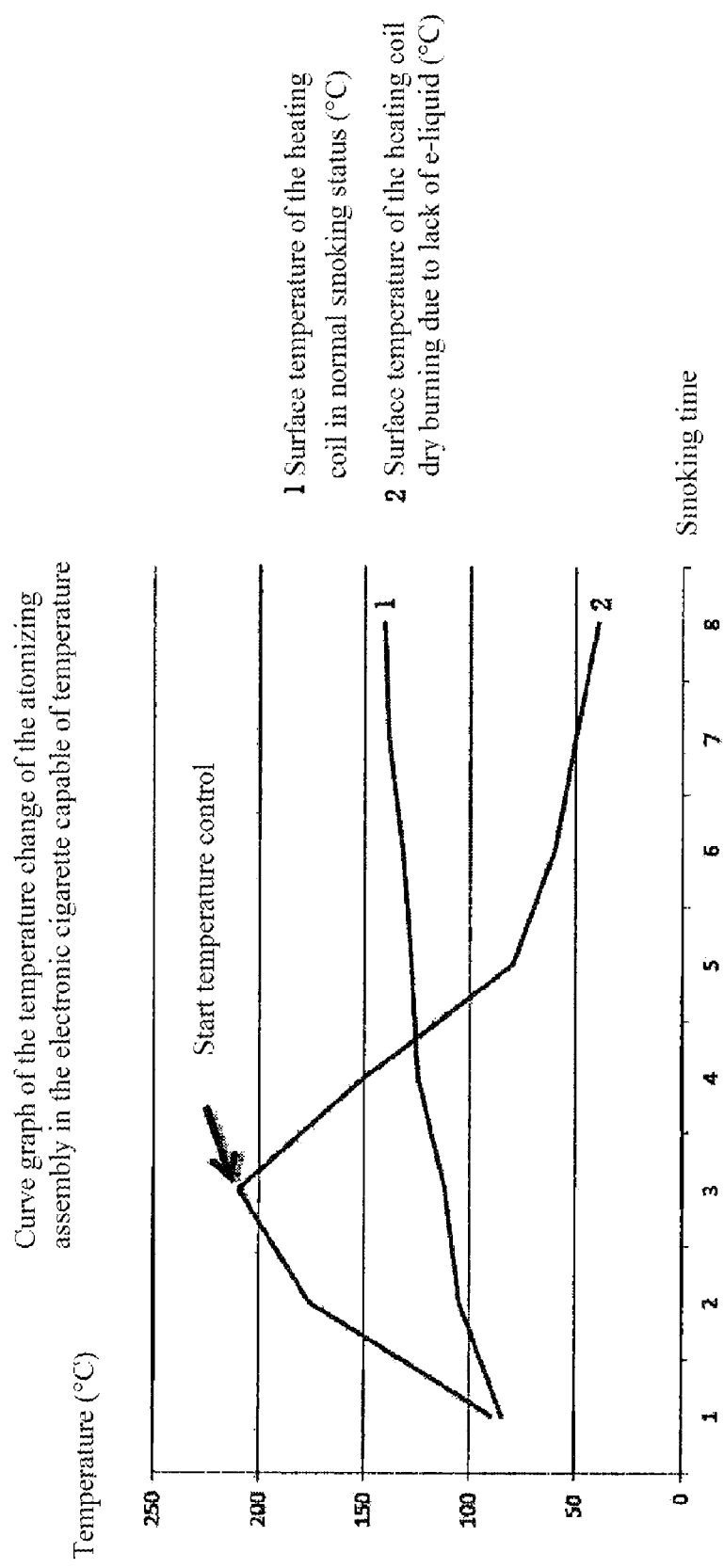
FIG. 6 is a curve graph showing the temperature change of a heating coil in an electronic cigarette capable of temperature control according to the present invention.

The present invention discloses an electronic cigarette capable of temperature control, as shown in FIG. 3, the electronic cigarette capable of temperature control comprises a casing 10, a liquid storage device 101 within the casing 10, an atomizing assembly (not shown), a power supply 102, and a circuit control board 103 provided with a smoking switch SW. Besides a heating coil and leads thereof (the heating coil and leads thereof are shown as an integral unit numbered 20 in FIG. 3, the atomizing assembly further comprises a liquid guiding element for guiding the e-liquid from the liquid storage device and the heating unit is a heating coil abutting the liquid guiding element. In the embodiment, the heating coil and the leads 20 thereof are made from thermo-sensitive material of which resistance varies along with the temperature in certain positive proportion. The circuit control board 103 comprises a power supply managing module 104, when the smoking switch SW is on, the power supply managing module 104 determines the corresponding temperature of the heating coil and the leads thereof by continuously detecting resistance of them, and sends corresponding control signal to make the heating coil connect to or disconnect from the power supply. As shown in FIGS. 3-4, the heating coil in FIG. 3 is exactly the resistor R in FIG. 4, both of them are unified as heating coil R hereinafter for convenience of understanding and illustration.

Specifically, as shown in FIG. 4, the power supply managing module 104 further comprises a chip U1, a triode Q4, a metal oxide semi-conductor field effect transistor M1, a third resistor R3, a fifth resistor R5, a sixth resistor R6, wherein:

the chip U1 has a number of pins, it can be seen in the FIG. 4 that the chip U1 has sixteen pins in total which are successively numbered from 1 to 16, the first pin is an on/off signal end KEY 1, the fourth pin is a power supply signal end BT+, the ninth pin is a control signal end HOT, the thirteenth pin is a grounding end and the sixteenth pin is a signal detecting end FB;

one end of the smoking switch SW is grounded while the other end thereof is connected to the end KEY 1;

one end of the third resistor R3 is connected to the end HOT while the other end thereof is connected to the base of the triode Q4; the emitter of the triode Q4 is grounded and between the base and the emitter thereof is provided a fourth resistor R4, the collector of the triode Q4 is connected to both the gate of the metal oxide semi-conductor field effect transistor M1 and one end of the fifth resistor R5, while both the other end of R5 and the source of the metal oxide semi-conductor field effect transistor M1 are connected to the end BT+;

the drain of the metal oxide semi-conductor field effect transistor M1 also acts as an end F+, one end of the heating coil R is connected to the end F+ while the other end thereof is grounded; one end of the sixth resistor R6 is grounded while the other end thereof and the drain of the metal oxide semi-conductor field effect transistor M1 are both connected to the end FB.

Moreover, the power supply managing module further comprises a seventh resistor R7 and a capacitor C1, wherein one end of the seventh resistor R7 is connected to the end FB while the other end thereof and one end of the capacitor C1 are connected and grounded, and the other end of the capacitor C1 is connected to the end BT+.

Still as shown in FIG. 4, the power supply managing module further comprises a first resistor R1, a second resistor R2, a first light emitting diode D1 and a second light emitting diode D2; the chip U1 further comprises a fifth pin and a sixth pin, wherein the fifth pin is connected to one end of the first resistor R1 and the other end of the first resistor R1 is connected to one end of the first light emitting diode D1, similarly, the sixth pin is connected to one end of the second resistor R2 and the other end of the second resistor R2 is connected to one end of the second light emitting diode D2, the other end of the first light emitting diode D1 and that of the second light emitting diode D2 are both grounded; when the power supply managing module detects a signal indicating temperature of the heating coil R is normal, the fifth pin of the chip U1 is powered to light the first light emitting diode D1 to indicate the electronic cigarette is in normal smoking status; otherwise, when the power supply managing module detects a signal indicating abnormal temperature of the heating coil R and disconnects it from the power supply, the sixth pin of the chip U1 is powered to light the second light emitting diode D2 to indicate a malfunction of dry burn is occurred in the electronic cigarette.

Figure 8:
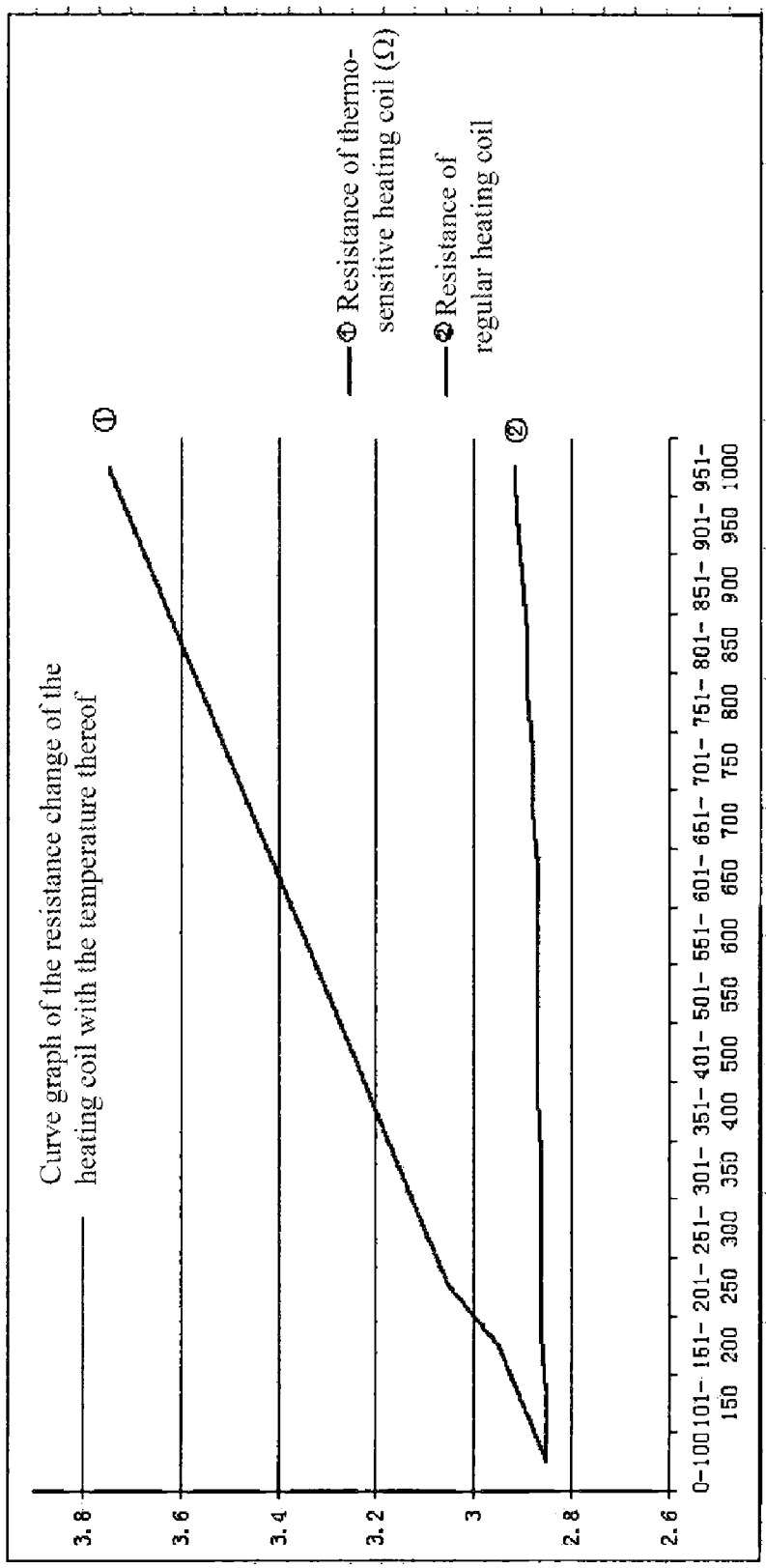
FIG. 8 is a curve graph showing a comparison between resistance of the heating coil according to the present invention and resistance of the regular heating coil.
Figure 9:
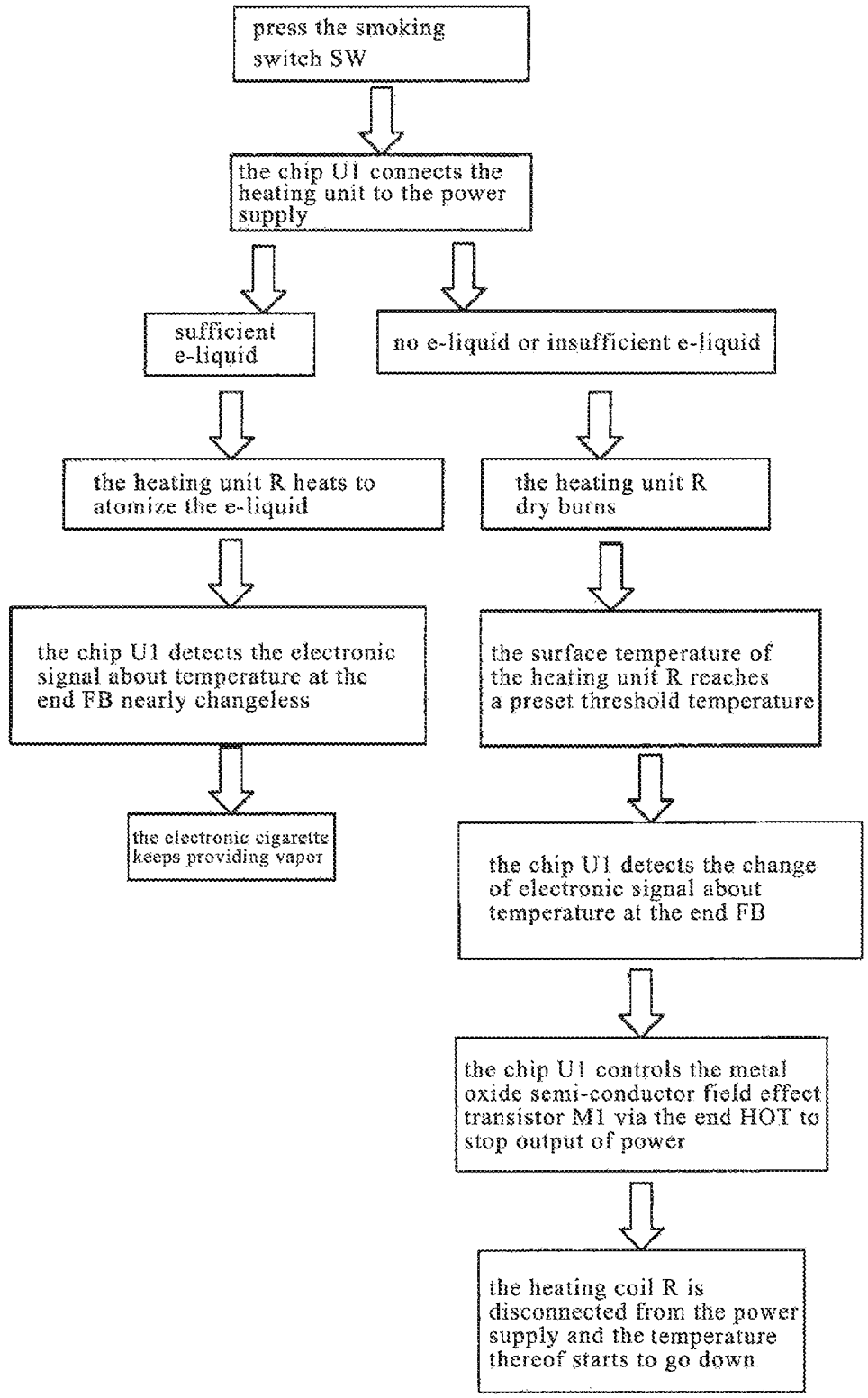
FIG. 9 is a flow diagram of the method for temperature control of the electronic cigarette capable of temperature control according to the present invention.

The detailed description of the operation process of the electronic cigarette capable of temperature control according to the present invention is given with reference to the circuit structure shown in FIG. 4, and FIGS. 5, 6 and 9. Specifically, the operation process of the electronic cigarette capable of temperature control, i.e. the method for temperature control of the electronic cigarette comprises the following steps:

S1: turning a smoking switch SW off and disconnecting a circuit control board from a power supply when the electronic cigarette is not in service;

S2: turning on the smoking switch SW when the user begins to smoke, sending a control signal via the end HOT according to a signal at an end KEY1 by a chip U1, connecting a heating coil R to the power supply via a metal oxide semi-conductor field effect transistor M1, starting to read electronic signals about temperature at an end FB by the chip U1, meanwhile, emitting light by the first light emitting diode D1;

S3: atomizing the e-liquid by the heating coil R when there is e-liquid in an atomizing assembly, during the process, the temperature of the heating coil R is stable and its resistance generally remains constant, the electronic signal about temperature at the end FB detected by the chip U1 stays constant, and the control signal sent via the end HOT by the chip U1 stays constant, and keeping providing vapor to the user, and keeping emitting light by the first light emitting diode D1; as shown in FIG. 5, the surface temperature of the heating coil R rises slowly as time goes on in this normal operation status, the surface temperature of the heating coil R is 141° C. in the $8^{th}$ minute; as shown in FIGS. 7-8, the resistance of the heating coil R stays nearly constant at that moment, only increases from 2.85Ω to 2.9Ω.

S4: controlling the metal oxide semi-conductor field effect transistor M1 by the chip U1 via the end HOT to disconnect the heating coil R from the power supply and stopping providing vapor to the user when the e-liquid in the atomizing assembly is used up or in shortage, the surface of the heating coil R dry burns, the temperature thereof goes up fiercely, the resistance of the heating coil R rises rapidly because the heating coil R is made from thermo-sensitive material with a positive temperature coefficient, as shown in FIGS. 7-8, and a change of the electronic signal about temperature at the end FB is detected by the chip U1, and then temperature of the heating coil R starts to go down; In the present embodiment, at the threshold temperature 210° C., the resistance of the heating coil R has reached 3.05Ω, at that time, a change of the electronic signal about temperature at the end FB is detected by the chip U1, and then the chip U1 controls the metal oxide semi-conductor field effect transistor M1 via the end HOT to disconnect the heating coil R from the power supply, the electronic cigarette stops providing vapor to the user, a second light emitting diode D2 emits light to indicate a malfunction and the temperature of the heating coil R starts to go down;

S5: cutting off the power supply immediately and indicating a malfunction by emitting light via the second light emitting diode D2 even if the smoking switch SW is turned on again by the user and the power supply is restored provisionally before the temperature of the heating coil R goes down below a preset threshold temperature 210° C. and e-liquid is supplemented to the atomizing assembly, as the electronic signal about temperature at the end FB detected by the chip U1 still is abnormal;

S6: supplying power to the heating coil R to atomizes the e-liquid normally and indicating a normal status by emitting light via the first light emitting diode D1 till the temperature of the heating coil R goes down below the preset threshold temperature 210° C., the e-liquid is supplemented to the atomizing assembly, the heating coil R returns its normal resistance and the user proceeds to smoke, and continuing supplying power to the heating coil R if the chip U1 detects the electronic signal about temperature at the end FB is normal.

Another method for temperature control according to embodiments of the present invention is as below: based on the preceding method, after the chip U1 detecting the electronic signal about temperature at the end FB, the comparison and determination is carried out on the basis of a preset rate of temperature change instead of the preset threshold temperature 210° C., for instance, when the rate of temperature change exceeds the preset value thereof 40° C. per second, the chip U1 controls the metal oxide semi-conductor field effect transistor M1 via the end HOT to disconnect the power supply from the heating coil R, the electronic cigarette stops providing vapor to the user.

Another embodiment of the present invention is as below: based on the preceding embodiment, the heating coil R is regular heating coil but the leads on the both ends thereof are made from thermo-sensitive material of which resistance varies along with the temperature in certain positive proportion, the temperature of the heating coil conducts quickly to the lead because of the connection therebetween, that is, the leads are capable of sensing the temperature of the heating coil, and thus the heating coil made from heat sensitive resistance material in the preceding embodiment may be replaced by the heating coil having leads made from heat sensitive resistance material.

Further, in still another embodiment, a heating coil characterized in that that both itself and the leads thereof are made from thermo-sensitive material of which resistance varies along with the temperature in certain positive proportion act as the heating coil R, the solution can replace any of the two preceding solutions to achieve identical technical effect.

In the steps 1 and 2 above, on and off of the smoking switch SW can be controlled manually, when user is to smoke, the smoking switch SW is turned on as the button thereof is pushed, and then the smoking switch SW is turned off as the button thereof is pushed again; besides, on and off of the smoking switch SW also can be realized by providing a pressure sensor inside the electronic cigarette, in this manner, when user is to smoke, the smoking switch SW is turned on or off automatically according to the change of pressure in the electronic cigarette detected by the pressure sensor. It should be noted that, on and off of the smoking switch SW definitely can be realized by other approaches, which don't need to be detailed one by one.

The circuit structure and method for temperature control of the present invention do well in temperature control of heating coil R within the electronic cigarette, and the problems such as over-temperature and burn out of the electronic cigarette due to dry-burn of the heating coil caused by the lack of e-liquid is effectively prevented, so does the problem that pernicious gas and burnt matter produced by dry-burn of the heating coil would be inhaled by users and threaten their health; besides, it brings no impact to the size of the electronic cigarette owing to its simple circuit, so it is adapted to be applied inside the electronic cigarette.

All the embodiments above are merely the preferred embodiments rather than limits of the present invention. The present invention is intended to cover various modifications and equivalent arrangements included within the principle and scope of the present invention.

What is claimed is:

1. An electronic cigarette capable of temperature control, comprising a casing, a liquid storage device within the casing, an atomizing assembly, a power supply, and a circuit control board provided with a smoking switch SW, the atomizing assembly comprises a heating unit and leads thereof, material of the heating unit and/or the leads is thermo-sensitive whose resistance varies along with the temperature in certain proportion, the circuit control board comprises a power supply managing module, when the smoking switch SW is on, the power supply managing module determines the corresponding temperature of the heating unit and the leads thereof by continuously detecting resistance of them, and sends corresponding control signal to make the heating unit and leads thereof connect to or disconnect from the power supply; characterized in that the power supply managing module further comprises a chip U1, a triode Q4, a metal oxide semi-conductor field effect transistor M1, a third resistor R3, a fifth resistor R5, a sixth resistor R6, wherein the chip U1 has a number of pins, wherein a first pin is an on/off signal end KEY 1, a fourth pin is a power supply signal end BT+, a ninth pin is a control signal end HOT, a thirteenth pin is a grounding end and a sixteenth pin is a signal detecting end FB; one end of the smoking switch SW is grounded while the other end thereof is connected to the end KEY 1; one end of the third resistor R3 is connected to the end HOT while the other end thereof is connected to the base of the triode Q4; the emitter of the triode Q4 is grounded and between the base and the emitter thereof is provided a fourth resistor R4, the collector of the triode Q4 is connected to both the gate of the metal oxide semi-conductor field effect transistor M1 and one end of the fifth resistor R5, while both the other end of R5 and the source of the metal oxide semi-conductor field effect transistor M1 are connected to the end BT+; the drain of the metal oxide semi-conductor field effect transistor M1 also acts as an end F+, one end of the heating unit and leads thereof is connected to the end F+ while the other end thereof is grounded; one end of the sixth resistor R6 is grounded while the other end thereof and the drain of the metal oxide semi-conductor field effect transistor M1 are both connected to the end FB.

2. The electronic cigarette capable of temperature control according to claim 1, characterized in that the power supply managing module further comprises a seventh resistor R7 and a capacitor C1, wherein one end of the seventh resistor R7 is connected to the end FB while the other end thereof and one end of the capacitor C1 are connected and grounded, and the other end of the capacitor C1 is connected to the end BT+.

3. The electronic cigarette capable of temperature control according to claim 1, characterized in that the material of the heating unit and/or the leads thereof is thermo-sensitive material with a positive temperature coefficient.

4. The electronic cigarette capable of temperature control according to claim 3, characterized in that the atomizing assembly further comprises a liquid guiding element for guiding the e-liquid from the liquid storage device and the heating unit is a heating coil abutting the liquid guiding element.

5. The electronic cigarette capable of temperature control according to claim 2, characterized in that the material of the heating unit and/or the leads thereof is thermo-sensitive material with a positive temperature coefficient.

6. The electronic cigarette capable of temperature control according to claim 5, characterized in that the atomizing assembly further comprises a liquid guiding element for guiding the e-liquid from the liquid storage device and the heating unit is a heating coil abutting the liquid guiding element.

7. The electronic cigarette capable of temperature control according to claim 2, characterized in that the power supply managing module further comprises a first resistor R1, a second resistor R2, a first light emitting diode D1 and a second light emitting diode D2; the chip U1 further comprises a fifth pin and a sixth pin, wherein the fifth pin is connected to one end of the first resistor R1 and the other end of the first resistor R1 is connected to one end of the first light emitting diode D1, similarly, the sixth pin is connected to one end of the second resistor R2 and the other end of the second resistor R2 is connected to one end of the second light emitting diode D2, the other end of the first light emitting diode D1 and that of the second light emitting diode D2 are both grounded; when the power supply managing module detects a signal indicating temperature of the heating unit and leads thereof is normal, the fifth pin of the chip U1 is powered to light the first light emitting diode D1 to indicate the electronic cigarette is in normal smoking status; otherwise, when the power supply managing module detects a signal indicating abnormal temperature of the heating unit and leads thereof and disconnects them from the power supply, the sixth pin of the chip U1 is powered to light the second light emitting diode D2 to indicate a malfunction of dry burn is occurred in the electronic cigarette.

8. The electronic cigarette capable of temperature control according to claim 7, characterized in that the material of the heating unit and/or the leads thereof is thermo-sensitive material with a positive temperature coefficient.

9. The electronic cigarette capable of temperature control according to claim 8, characterized in that the atomizing assembly further comprises a liquid guiding element for guiding the e-liquid from the liquid storage device and the heating unit is a heating coil abutting the liquid guiding element.

10. A method for controlling the temperature of an electronic cigarette, comprising the following steps:
S1: turning a smoking switch SW off and disconnecting a circuit control board from a power supply when the electronic cigarette is not in service;
S2: turning on the smoking switch SW when the user begins to smoke, sending a control signal via the end HOT according to a signal at an end KEY1 by a chip U1, connecting a heating coil R to the power supply via a metal oxide semi-conductor field effect transistor M1, starting to read electronic signals about temperature at an end FB by the chip U1;
S3: atomizing the e-liquid by the heating coil R when there is e-liquid in an atomizing assembly, during the process, the temperature of the heating coil R is stable and its resistance generally remains constant, the electronic signal about temperature at the end FB detected by the chip U1 stays constant, and the control signal sent via the end HOT by the chip U1 stays constant, and keeping providing vapor to the user;
S4: controlling the metal oxide semi-conductor field effect transistor M1 by the chip U1 via the end HOT to disconnect the heating coil R from the power supply and stopping providing vapor to the user when the e-liquid in the atomizing assembly is used up or in shortage, the surface of the heating coil R dry burns, the temperature thereof goes up fiercely, the resistance of the heating coil R rises rapidly because the heating coil R is made from thermo-sensitive material with a positive temperature coefficient and a change of the electronic signal about temperature at the end FB is detected by the chip U1, and then temperature of the heating coil R starts to go down;
S5: cutting off the power supply immediately even if the smoking switch SW is turned on again by the user and the power supply is restored provisionally before the temperature of the heating coil R goes down to a preset threshold temperature 210° C. and e-liquid is supplemented to the atomizing assembly, as the electronic signal about temperature at the end FB detected by the chip U1 still is abnormal;
S6: supplying power to the heating coil R to atomizes the e-liquid normally till the temperature of the heating coil R goes down below the preset threshold temperature 210° C., the e-liquid is supplemented to the atomizing assembly, the heating coil R returns its normal resistance and the user proceeds to smoke, and continuing supplying power to the heating coil R if the chip U1 detects the electronic signal about temperature at the end FB is normal.

11. A method for controlling the temperature of an electronic cigarette, characterized in that comprising the following steps:
S1: turning a smoking switch SW off and disconnecting a circuit control board from a power supply when the electronic cigarette is not in service;
S2: turning on the smoking switch SW when the user begins to smoke, sending a control signal via the end HOT according to a signal at an end KEY1 by a chip U1, connecting a heating coil R to the power supply via a metal oxide semi-conductor field effect transistor M1, starting to read electronic signals about temperature at an end FB by the chip U1;

S3: atomizing the e-liquid by the heating coil R when there is e-liquid in an atomizing assembly, during the process, the temperature of the heating coil R is stable and its resistance generally remains constant, a rate of temperature change at the end FB detected by the chip U1 is lower than a preset rate of temperature change, and the control signal sent via the end HOT by the chip U1 stays constant, and keeping providing vapor to the user;

S4: controlling the metal oxide semi-conductor field effect transistor M1 by the chip U1 via the end HOT to disconnect the heating coil R from the power supply and stopping providing vapor to the user when the e-liquid in the atomizing assembly is used up or in shortage, the surface of the heating coil R dry burns, the temperature thereof goes up fiercely, the resistance of the heating coil R rises rapidly because the heating coil R is made from thermo-sensitive material with a positive temperature coefficient and the rate of temperature change at the end FB detected by the chip U1 exceeds the preset rate of temperature change, and then temperature of the heating coil R starts to go down;

S5: cutting off the power supply immediately even if the smoking switch SW is turned on again by the user and the power supply is restored provisionally before the rate of temperature change of the heating coil R goes down to the preset rate of temperature change and e-liquid is supplemented to the atomizing assembly, as the rate of temperature change at the end FB detected by the chip U1 still exceeds the preset rate of temperature change;

S6: supplying power to the heating coil R to atomizes the e-liquid normally till the rate of temperature change of the heating coil R goes down below the preset rate of temperature change, the e-liquid is supplemented to the atomizing assembly, the heating coil R returns its normal resistance and the user proceeds to smoke, and continuing supplying power to the heating coil R if the chip U1 detects the rate of temperature change at the end FB is normal.

* * * * *